United States Patent [19]
Gibbs

[11] Patent Number: 5,732,882
[45] Date of Patent: Mar. 31, 1998

[54] AIR FRESHENER AND CHAIN PULL DEVICE FOR CEILING FAN

[75] Inventor: George S. Gibbs, Thomasville, Ga.

[73] Assignee: New Ideas International, Inc., Thomasville, Ga.

[21] Appl. No.: 518,800

[22] Filed: Aug. 24, 1995

[51] Int. Cl.$^6$ ............................................. A61L 9/04
[52] U.S. Cl. ........................... 239/56; 239/57; 239/289
[58] Field of Search .......................... 239/53, 56, 57, 239/289; 261/84, DIG. 65

[56] References Cited

U.S. PATENT DOCUMENTS

| | | | |
|---|---|---|---|
| D. 247,249 | 2/1978 | Schimanski | D23/150 |
| 2,579,715 | 12/1951 | Wilson et al. | 239/57 |
| 3,087,679 | 4/1963 | Wilson | 239/57 |
| 3,552,632 | 1/1971 | Wilson | 239/57 X |
| 3,844,478 | 10/1974 | Davis | 239/57 |
| 4,219,145 | 8/1980 | Jaeschke et al. | 229/8 |
| 4,361,279 | 11/1982 | Beacham | 239/56 |
| 4,753,573 | 6/1988 | McKnight | 416/62 |
| 4,889,543 | 12/1989 | Burt | 55/97 |
| 4,944,898 | 7/1990 | Glaser | 261/84 |
| 4,960,240 | 10/1990 | McElfresh | 239/56 |
| 5,022,819 | 6/1991 | Murcin et al. | 416/62 |

*Primary Examiner*—Andres Kashnikow
*Assistant Examiner*—Steven J. Ganey
*Attorney, Agent, or Firm*—Kennedy, Davis & Kennedy

[57] ABSTRACT

An air freshener device disposed in proximity to a ceiling fan by attachment to a pull chain of the ceiling fan for scenting air moved by the fan. The device has a unitary clam-shell housing for receiving a scented pad between a first dish and a second dish which join together by an intermediate foldable hinge. The dishes define a plurality of vent openings for passage of air therethrough for scenting. A latch member extending laterally from the first dish defines a channel for lockingly engaging a post that extends radially inwardly on the second dish upon folding the dishes together along the hinge. A pair of oppositely aligned slots in portions of the first dish receiving links of the pull chain for securing the device in close proximity to the ceiling fan and for overlying the scented pad in the housing.

4 Claims, 2 Drawing Sheets

AIR FRESHENER AND CHAIN PULL DEVICE FOR CEILING FAN

TECHNICAL FIELD

The present invention relates to ceiling fans. More particularly, the present invention relates to devices scenting air moved by ceiling fans.

BACKGROUND OF THE INVENTION

Ceiling fans have become popular additions to rooms of homes and restaurants, in part for decoration and in part for economical movement of air for both cooling and heating seasons. The ceiling fans typically have an electric motor that mounts to a bracket rigidly connected to the ceiling. A plurality of fan blades attach to a rotatable ring that is operatively coupled to the electric motor. The fan blades generally mount at an acute angle relative to horizontal, for pushing air on the surfaces of the blades as the motor rotates the ring. During warm weather, the fans rotate in a first direction to push air downwardly upwardly towards the floor in order to induce circulation of the cooler air near the floor. During cold weather, the fans rotate in a second opposite direction to push air upwardly towards to the ceiling in order to induce circulation of the warmer air near the ceiling. The circulation of air creates a desirable cooling or warming effect.

In addition to use of ceiling fans to circulate air, the use of devices that emit an air scenting fragrance has In addition to use of ceiling fans to circulate air, the use of devices that emit an air scenting fragrance has increased. Releasing fragrance in to ambient air has the effect of deodorizing and freshening the air. Often such devices have housings for positioning the scent emissive material statically in a room. Other devices warm a scented material to induce the fragrance in to the air of a room. The scented material typically comprises an evaporative solid or liquid.

While these scent emissive devices have accomplished the scenting of air, there are problems associated with their use. In particular, the scent emissive devices often are placed away from moving air, such as adjacent a wall socket near a floor or on a shelf adjacent a side wall of the room. The devices thereby are less directly exposed to moving air and contact relatively static air. The distribution of scent is thereby limited and reduces the effectiveness of the scenting for a room.

It is thus seen that a need exists for an improved scent-emissive device for disposing in proximity to ceiling fans for scenting air placed in motion by the fans. It is to the provision of such that the present invention is primarily directed.

SUMMARY OF THE INVENTION

The present invention comprises an air freshener apparatus for engagement to a pull-chain of a ceiling fan. The apparatus has a unitary clam-shell housing of a first dish and a second dish joined together by an intermediate foldable hinge. Each dish includes a skirt that extends a predetermined distance laterally from a perimeter edge. The skirts include relatively offset notched portions on distal edges for mating engagement of the dishes. Each dish also defines a plurality of vent openings for passage of air therethrough. A latch member extends laterally from the skirt on the second dish. The post is aligned with respect to the latch member for being received in the channel upon folding the dishes together along the hinge. A plurality of locating ribs extend from an interior surface of the first dish for guidingly locating perimeter edges of a scented pad received therein. A pair of oppositely aligned slots in portions of the skirt of the first dish receive segments of a pull chain of a ceiling fan. This secures the air freshening device to the pull chain and the pull chain thereby overlies the scented pad in the first dish for securing the pad therein. The clam-shell housing, receiving the scented pad between the first dish and second dish, attaches to the pull chain by entering segments of the chain into the slots and thereby overlying the pad. The housing locks closed by engaging the post in the channel upon folding the first and second dishes together along the hinge with mating engagement of the notched distal edges of the dishes.

DETAILED DESCRIPTION

Figure 1:
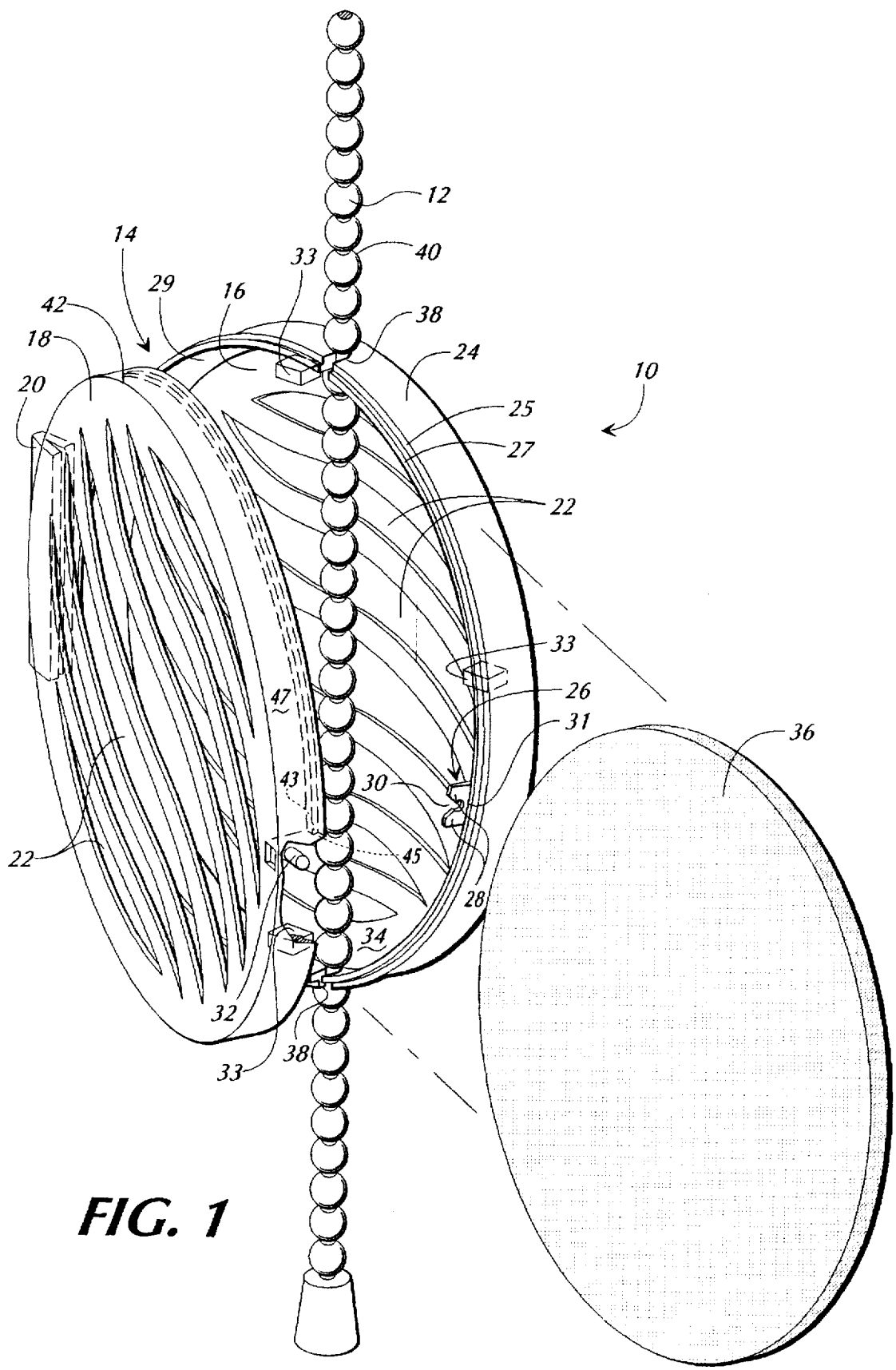
FIG. 1 is a perspective view of an air freshening device for holding a scent-emissive pad in proximity to a ceiling fan according to the present invention.
Figure 2:
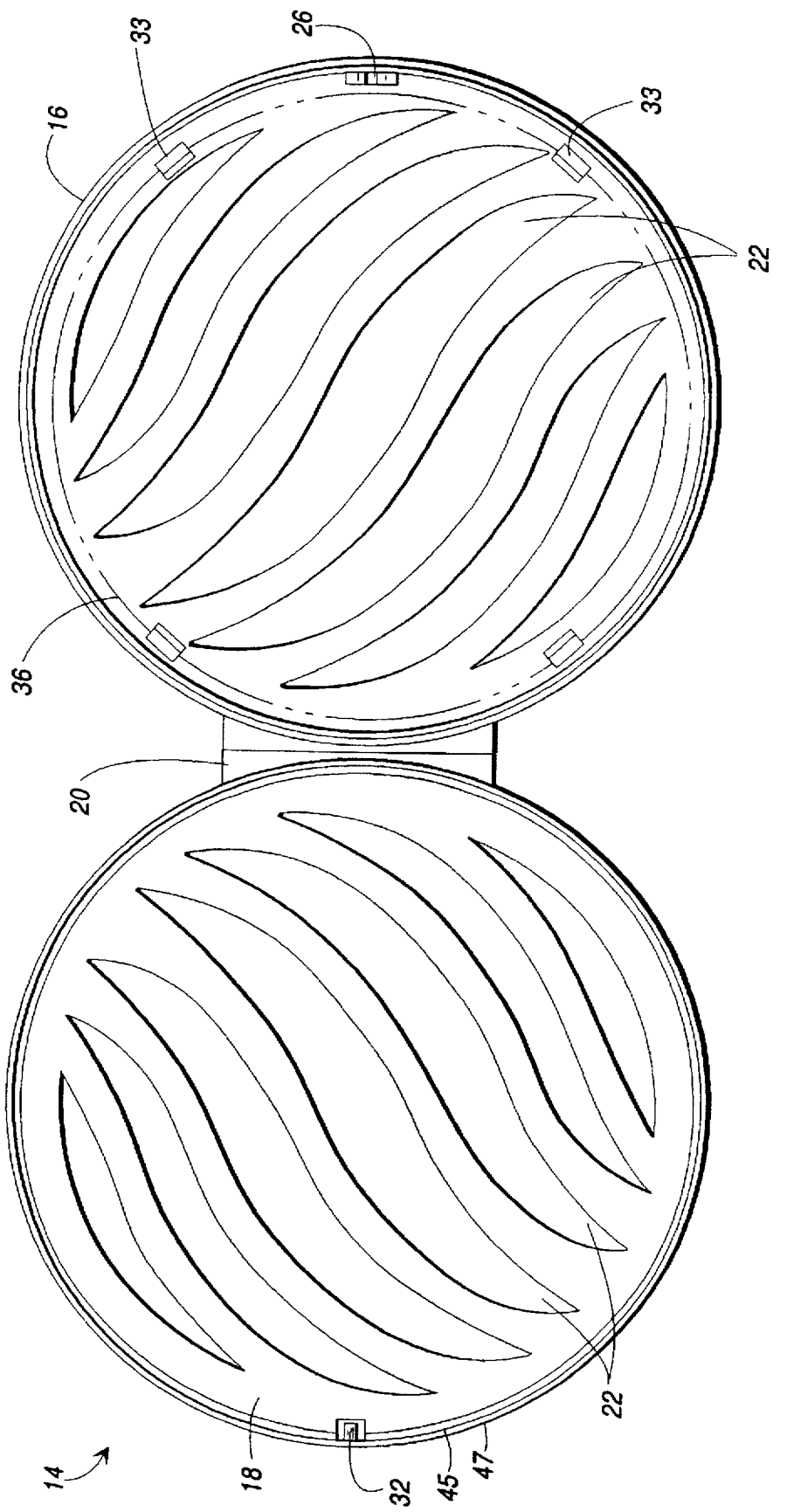
FIG. 2 is a plan view of the air freshening device illustrated in FIG. 1.

Referring now in more detail to the drawings which illustrate an air freshener device 10 for engagement to a pull-chain 12 of a ceiling fan (not illustrated). The air freshener apparatus 10 comprises a unitary clam-shell housing 14 having a first dish 16 and a second dish 18 joined together by an intermediate foldable hinge 20. Each dish 16 and 18 defines a plurality of vent openings 22 for passage of air therethrough. A skirt 24 extends laterally a predetermined distance from the dish 16 around a perimeter edge. A distal edge of the skirt 24 defines a recessed notch 25 wherein the thickness of the outwardly extending wall 27 is of a reduced thickness relative the thickness of the skirt. In the illustrated embodiment, the wall 27 is collinear with an inner face 29 of the skirt 24.

A latch member 26 extends laterally from the first dish 16 on the skirt 24. A pair of arms 28 extend outwardly at an angle and define a channel 30 for receiving a post 32 into a notch 31.

The dish 16 includes a plurality of locating ribs 33 that are upstanding from an interior surface 34 for guidingly locating edges of a scented pad 36 received therein. A pair of oppositely aligned slots 38 in portions of the skirt 24 of the first dish 16 receive links 40 of the pull-chain 12 of the ceiling fan. The pull chain 12 thereby overlies the scented pad 36 in the first dish 16 for securing the scented pad therein.

A skirt 42 extends laterally a predetermined distance from the dish 18 around a perimeter edge. A distal edge of the skirt 42 defines a recessed notch 43 wherein the thickness of the outwardly extending wall 45 is of reduced thickness relative the thickness of the skirt 42. The wall 45 in the illustrated embodiment is collinear with an outer face 47 of the skirt 42. The notches 25 and 43 matingly engage when the clam shell dishes 16 and 18 are closed together, as discussed below. The notches 25 and 43 are preferably one-half the thickness of the skirts 24 and 42.

The post 32 extends radially inwardly from the skirt 42 of the dish 18. The post 32 is aligned on the skirt 42 with respect to the latch member 26 on the skirt 24 for being received through the channel 30 and into the notch 31 upon folding the dishes 16 and 18 together along the hinge 20.

In use, the housing 10 holds the scent-emissive pad 36 and connects to the chain 12 of the ceiling fan. In a preferred embodiment, the scent-emissive pad comprises a foam substrate that holds a carrier material and an evaporative fragrance. The carrier material and evaporative fragrance preferably are homogeneously blended together and applied to the foam substrate. The air freshening device is preferably molded of a resilient plastic material. The scented pad 36 is positioned in the first dish 16 juxtaposed to the locating ribs 33 that abut the edges of the pad. The locating ribs 33 guide the placed of the scented rib 36 in the first dish 16. A portion of the pull-chain 12 is slippingly engaged to one of the slots 38 in the first dish 16 by introducing one of the links 40 into the slot. The pull chain 12 overlies the scented pad 36, and a second portion of the pull-chain is slippingly engaged to the second slot in the dish 16. The dishes 16 and 18 are then closed together by folding the device 10 on the hinge 20. This brings the post 32 into the channel 30 which guides the post into engagement with the notch 31, thereby locking the clam-shell housing 14 together. The air freshening device 10 then hangs a short distance below the ceiling fan in proximity of air circulated by the fan.

The openings 22 in the dishes 16 and 18 allow air circulated by the ceiling fan to contact the scent-emissive pad 36. The evaporative fragrance migrates through the carrier pad 36 to its surfaces where the circulating air becomes scented by passing in contact with the pad. The housing 14 is securely held to the pull chain 12 by the slots 38. The ceiling fan thereafter can be operated by grasping the air freshening device 10 in order to pull the chain 12 to operate the ceiling fan.

The foregoing has disclosed an improved air freshener and chain puller device for operating a ceiling fan and scenting the air moved thereby. It should be understood that the above described embodiments merely illustrate principles of the invention in preferred forms. Many modifications, additions, and deletions may, of course, be made thereto without departure from the spirit and scope of the invention as set forth in the following claims.

What is claimed is:

1. An air freshener apparatus for engagement to a pull-chain of a ceiling fan, comprising:

a unitary clam-shell housing for receiving therein a scented pad, the housing having a first dish and a second dish joined together by an intermediate foldable hinge, each dish including a skirt extending a predetermined distance laterally from a perimeter edge, the dishes defining a plurality of vent openings for passage of air therethrough;

a latch member extending laterally from the first dish on the skirt and defining a channel therein;

a post extending radially inwardly from the skirt on the second dish aligned thereon with respect to the latch member for being received in the channel upon folding the dishes together along the hinge; and a pair of oppositely aligned slots in portions of the skirt of the first dish for receiving segments of a pull chain of a ceiling fan for overlying the scented pad in the housing, whereby the clam-shell housing, receiving the scented pad between the first dish and second dish, attaches to the pull chain by entering segments of the chain into the slots thereby overlying the pad and locks closed by engaging the post in the channel upon folding the first and second dishes together along the hinge.

2. The air freshener apparatus as recited in claim 1, wherein:

the distal edge of the skirt on the first dish defines a first recessed notch; and the distal edge of the skirt on the second dish defines a second recessed notch offset relative the first notch, whereby the offset notches matingly engage upon folding the first and second dishes together along the hinge.

3. An air freshener apparatus for engagement to a pull-chain of a ceiling fan, comprising:

a unitary clam-shell housing for receiving therein a scented pad, the housing having a first dish and a second dish joined together by an intermediate foldable hinge, each dish including a skirt extending a predetermined distance laterally from a perimeter edge, the dishes defining a plurality of vent openings for passage of air therethrough;

a latch member extending laterally from the first dish on the skirt and defining a channel therein;

a post extending radially inwardly from the skirt on the second dish aligned thereon with respect to the latch member for being received in the channel upon folding the dishes together along the hinge;

a plurality of locating ribs upstanding from an interior surface of the first dish for guidingly locating edges of the scented pad received therein; and a pair of oppositely aligned slots in portions of the skirt of the first dish for receiving segments of a pull chain of a ceiling fan for overlying the scented pad in the housing, whereby the clam-shell housing, receiving the scented pad between the first dish and second dish, attaches to the pull chain by entering segments of the chain into the slots thereby overlying the pad and locks closed by engaging the post in the channel upon folding the first and second dishes together along the hinge.

4. The air freshener apparatus as recited in claim 3, wherein:

the distal edge of the skirt on the first dish defines a first recessed notch; and the distal edge of the skirt on the second dish defines a second recessed notch offset relative the first notch, whereby the offset notches matingly engage upon folding the first and second dishes together along the hinge.

* * * * *